United States Patent
Leo et al.

(10) Patent No.: US 6,451,046 B1
(45) Date of Patent: Sep. 17, 2002

(54) FACIAL ICEPACK

(76) Inventors: Dan Leo, 300 E. 40th St. #32B, New York, NY (US) 10016; Alan Winter, c/o Dan Leo 300 E. 40th St. #32B, New York, NY (US) 10016

( * ) Notice: Subject to any disclaimer, the term of this patent is extended or adjusted under 35 U.S.C. 154(b) by 0 days.

(21) Appl. No.: 09/898,593

(22) Filed: Jul. 5, 2001

(51) Int. Cl.⁷ .................................................. A61F 7/00
(52) U.S. Cl. ...................... 607/109; 607/112; 607/114; 602/2
(58) Field of Search .................. 607/108–110, 112, 607/114; 602/14, 2

(56) References Cited

U.S. PATENT DOCUMENTS

| | | | | |
|---|---|---|---|---|
| 4,190,054 A | * | 2/1980 | Brennan | 607/112 |
| 4,765,338 A | * | 8/1988 | Turner et al. | 607/110 |
| 5,020,536 A | * | 6/1991 | Keen | 607/109 |
| 5,188,103 A | * | 2/1993 | Smith | 607/109 |
| 5,837,004 A | * | 11/1998 | Lavore | 607/109 |
| 6,261,314 B1 | * | 7/2001 | Rich | 607/109 |

* cited by examiner

Primary Examiner—Michael A. Brown
Assistant Examiner—Lalita M. Hamilton
(74) Attorney, Agent, or Firm—Charles E. Temko

(57) ABSTRACT

A device for holding an icepack or other heat transfer means on various parts of the face of a user including an elastic headband strap adjustably secured by hook and pile interconnection, and a second strap which interconnects with the headband at both ends with hook and pile interconnection, which supports the icepack.

2 Claims, 1 Drawing Sheet

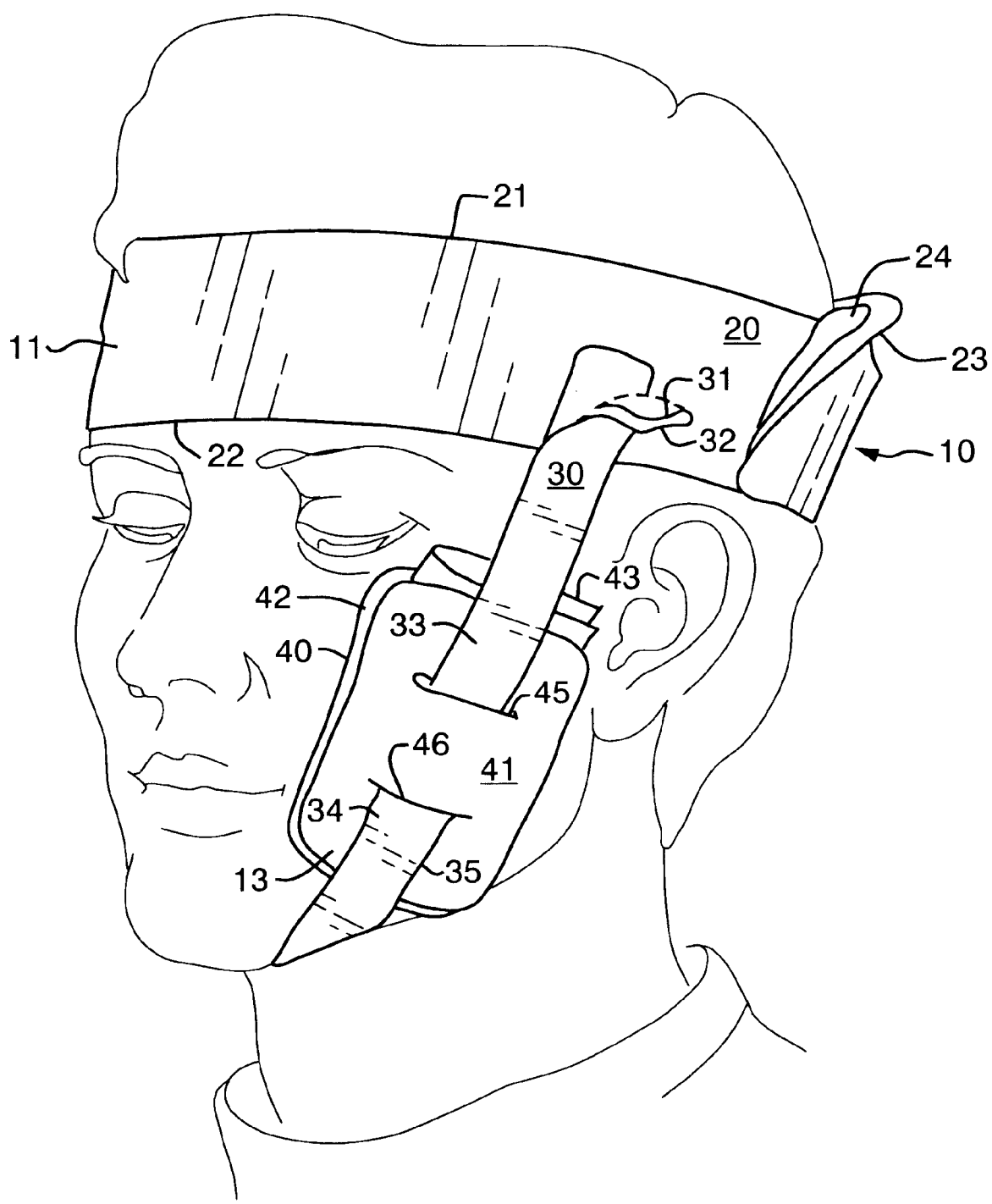

FACIAL ICEPACK

BACKGROUND OF THE INVENTION

This invention relates generally to the field of surgical bandages and similar devices, and more particularly to an improved device for supporting an icepack or other heat transfer means on various surfaces of the face or under the chin of a user.

Various ailments or particular types of trauma are responsive to a cold compress which can reduce swelling and pain over short periods of time. Where the area to be treated is on an arm or leg, the fastening of a cold compress is a relatively simple matter. In the case of a facial trauma, for example, after extensive dental treatment, such compress must be usually manually maintained in position by the user, which at least partially reduces the ability of the user to perform two-handed tasks.

SUMMARY OF THE INVENTION

Briefly stated, the invention contemplates the provision of an improved elastic device including selectively adjustable components which enable the positioning and maintenance of an icepack or other treatment element over virtually any portion of the face or under chin area without the use of an adhesive. To this end, the disclosed device includes a first band element of elastic material adjustable in length using hook and pile interconnections which surround the head of the user above the face. A second band element is of similar material, and includes hook and pile interconnecting means for engaging the first band. The second band adjustably supports a carrier containing a chilled or frozen component which is adapted to contact the face or under chin area in virtually any position.

BRIEF DESCRIPTION OF THE DRAWING

In the drawing, to which reference will be made in the specification, FIG. 1 is a perspective view of an embodiment of the invention.

DETAILED DESCRIPTION OF THE DISCLOSED EMBODIMENT

In accordance with the invention, the device, generally indicated by reference character 10, comprises broadly: a first band element 11, a second band element 12, and a pouch element 13.

The first band element 11 is formed of elastic material including a front surface 20, having an engageable pile, first and second longitudinal edges 21 and 22, first and second end edges, one of which is indicated by reference character 23, and a back surface 24, having hook material at the ends thereof for engaging the surface 20 in adjusted position.

The second band element 12 is somewhat narrower and may be made of the same elastic material. Adjacent a first end 30 is a hooked surface 31. The opposite end (not shown) may be similarly equipped or may be permanently fastened to the first band element 11. The band 12 also includes an outer surface 33, and longitudinal edges 34 and 35. The end 31 may be attached at any point to the outer surface of the band 11.

The pouch element 13 is preferably of synthetic resinous laminous construction, and includes a first lamina 40 and a second lamina 41 forming an interstice 42 for the reception of cooling material 43. This may be a small synthetic resinous bag containing fluid coolant known in the art, the bag being foldable to form overall dimensions corresponding to the interstice 42. In the event that this material is not available, refrigerated ice cubes, either whole or crushed, by also be used. The lamina 41 includes first and second slots 45 and 46 for engagement by the second band element 12 which enable the pouch element to be selectively adjusted in a sliding manner to almost any point along the second band element.

Should the place of cold application be located above the eyes and ears on the head of the user, it is possible to disconnect the pouch element 13 from the second band element 12, and position it beneath the first band element 11 at any desired location. With such arrangement, the second band element 12 serves to maintain the first band element in its proper position.

The device may be installed and removed as often as necessary, without the use of any adhesives or any components requiring replacement. Because adjustment of both first and second band elements is on a continuous basis, the adjustment may be performed at the time of installation.

We wish it to be understood that we do not consider the invention to be limited to the precise details of structure shown and described in the specification, for obvious modifications will occur to those skilled in the art to which the invention pertains.

We claim:

1. A device for holding a heat exchanging pouch in position upon various surfaces of the face and head of a user comprising: a first elastic elongated band element of length sufficient to surround the head of said user, said band element having inner and outer surfaces, at least some areas of which have hook and interconnecting means, said first band element being adapted to surround the head of a user above the facial areas thereof; a second elongated band element selectively interconnectible at at least one end thereof to said surface of said first band element by hook and interconnecting means, and adapted to be positioned beneath the chin; and a pouch element selectively positioned on said second band element and slightably adjustable therealong to overlie a predetermined area of the face of said user; said pouch element having a pair of laminated planar members defining an interstice for retaining a heat transfer material, and first and second slots in one of said pair of laminated members for passage of said band element there through whereby said pouch element may be slightably adjustable therealong while said device is in engaged condition with said user.

2. A device in accordance with claim 1 in which said pouch element is detachable from said second band element for positioning beneath said first band element.

* * * * *